(12) United States Patent
Williams et al.

(10) Patent No.: US 6,504,027 B1
(45) Date of Patent: *Jan. 7, 2003

(54) DECARBOXYLATION PROCESS FOR SYNTHESIZING CARBAPENEM ANTIBIOTICS

(75) Inventors: John M. Williams, Belle Mead; Karel M. J. Brands, Hoboken, both of NJ (US); Renato T. Skerlj, Blaine, WA (US); Peter Houghton, Scotch Plains, NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 218 days.

(21) Appl. No.: 09/487,044

(22) Filed: Jan. 19, 2000

Related U.S. Application Data

(63) Continuation of application No. 09/252,290, filed on Feb. 18, 1999, now abandoned.
(60) Provisional application No. 60/076,829, filed on Mar. 2, 1998.

(51) Int. Cl.[7] ............... C07D 477/20; A61P 31/04; A61K 31/407
(52) U.S. Cl. ............................................. 540/350
(58) Field of Search ................. 540/350; 514/210.12

(56) References Cited

U.S. PATENT DOCUMENTS

| | | | | |
|---|---|---|---|---|
| 4,269,772 A | | 5/1981 | Melillo et al. ............... | 540/350 |
| 4,350,631 A | | 9/1982 | Christensen et al. ........ | 540/350 |
| 4,383,946 A | | 5/1983 | Christensen et al. ........ | 546/272 |
| 4,414,155 A | | 11/1983 | Liu et al. .................... | 540/350 |
| 4,994,568 A | | 2/1991 | Christensen ................ | 540/350 |
| 5,034,384 A | | 7/1991 | Greenlee et al. ............ | 514/210 |
| 5,478,820 A | | 12/1995 | Betts et al. .................. | 514/210 |
| 5,952,323 A | * | 9/1999 | Zimmerman ................ | 514/210 |
| 6,063,931 A1 | * | 1/2001 | Brands ........................ | 548/411 |
| 6,180,783 B1 | * | 1/2001 | Williams ..................... | 540/350 |

FOREIGN PATENT DOCUMENTS

| | | |
|---|---|---|
| EP | 472062 | 2/1992 |
| WO | WO97/45430 | 5/1997 |

OTHER PUBLICATIONS

L. M. Fuentes et al., *J. Am. Chem. Soc.*, 108, p 4670–4676 (1986).
C. Wentrup et al., *J. Am. Chem. Soc.*, 108, p 6161–6183 (1980).
D. G. Melillo et al., *Tet. Ltrs.* (21) p 2783 (1980).
S. M. Berg et al., *J. Pharm. Sci.*, 66(1), p 1–16 (1977).

* cited by examiner

*Primary Examiner*—Mark L Berch
(74) *Attorney, Agent, or Firm*—Sylvia A. Ayler; Mark R. Daniel

(57) ABSTRACT

A process for the direct crystallization of a compound of the formula I:

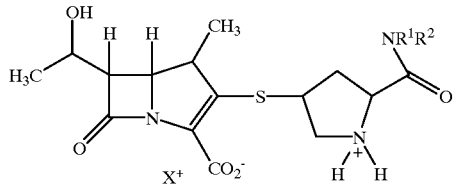

or a pharmaceutically acceptable salt thereof, is disclosed, wherein $R^1$ and $R^2$ represent H, $C_{1-10}$ alkyl, aryl or heteroaryl, or substituted $C_{1-10}$ alkyl, aryl or heteroaryl and $X^+$ represents a charge balancing group, comprising extracting a solution containing a crude compound of formula I or Ia:

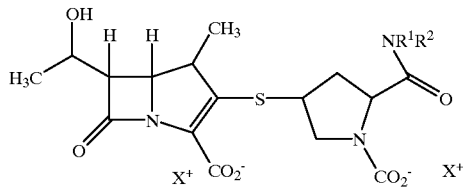

or a pharmaceutically acceptable salt thereof, wherein each X+ is a charge balancing group, and R1 and R2 are as described above with a C4–10 alcohol, collecting and crystallizing the resulting aqueous phase to produce a crystalline compound of formula I.

10 Claims, No Drawings

DECARBOXYLATION PROCESS FOR SYNTHESIZING CARBAPENEM ANTIBIOTICS

This application is a continuation of U.S. patent application Ser. No. 09/252,290, filed Feb. 18, 1999, which is Provisional Application No. 60/076,829, filed on Mar. 2, 1998.

BACKGROUND OF THE INVENTION

In the past purification and isolation of the compound of formulae I and II were achieved via a combination of several operations: extractions using solvents such as dichloromethane to remove residual organic solvents, chromatography using hydrophobic resins, nanofiltration for concentration of the process stream followed by crystallization of the pure drug. Several of these operations require high capital expenditure. In addition, the time-cycle of such a process is relatively long compromising the quality of the carbapenem product.

The object of the present invention is to teach a much simplified isolation protocol of the compound of formulae I and II via extractions with an alcohol with or without containing an appropriate ion-pairing reagent which concomitantly concentrates the carbapenem compounds followed by a direct crystallization of the product. The present invention is a more practical, efficient, safer and cost effective process because it eliminates the time consuming (and capital intensive) column purification and nanofiltration steps which can compromise the quality of the carbapenem compound due to degradation.

These and other objects will be apparent from the teachings contained herein.

SUMMARY OF THE INVENTION

A process for the direct crystallization of a compound of the formula I:

I

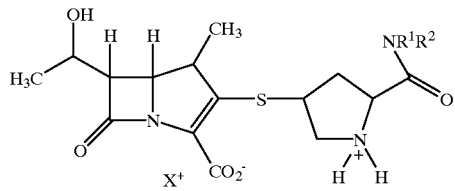

or a pharmaceutically acceptable salt thereof, is disclosed, wherein $R^1$ and $R^2$ represent H, $C_{1-10}$ alkyl, aryl or heteroaryl, or substituted $C_{1-10}$ alkyl, aryl or heteroaryl and $X^+$ represents a charge balancing group, comprising extracting a solution containing a crude compound of formula I or Ia:

Ia

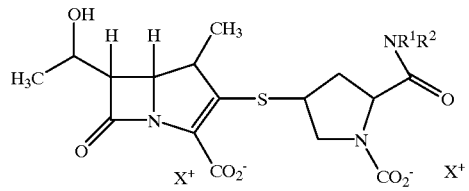

or a pharmaceutically acceptable salt thereof, wherein each X+ is a charge balancing group, and R1 and R2 are as described above with a C4–10 alcohol, collecting and crystallizing the resulting aqueous phase to produce a crystalline compound of formula I.

DETAILED DESCRIPTION OF THE INVENTION

Carbapenems can be prepared by coupling the, appropriate sidechain to a protected enolphosphate (3). In this reaction a base and solvent are used. The resulting crude product can then be deprotected to give the desired carbapenem in its crude form. In order to isolate this product in pure form via crystallization sideproducts and solvents need to be removed and the concentration of the product increased. In the past this has been typically achieved via a combination of extraction, column chromatography and nanofiltration.

It has now been discovered that the column chromatography and nanofiltration operations can be eliminated when the extraction is carried out with an appropriate alcohol. A preferred extraction is carried out with the appropriate alcohol in the presence of an ion-pairing reagent. The process described herein allows a direct crystallization of carbapenem compounds after this type of extraction. The process eliminates the column purification step and replaces the nanofiltration step for concentration of the carbapenem compound in preparation for the crystallization step.

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight or branched, and when of sufficient size, e.g., $C_{3-15}$ may be cyclic. Preferred straight or branched alkyl groups include methyl, ethyl, propyl, isopropyl, butyl and t-butyl. Preferred cycloalkyl groups include cyclopropyl, cyclopentyl and cyclohexyl.

Alkyl also includes an alkyl group substituted with a cycloalkyl group, such as cyclopropylmethyl.

Alkyl also includes a straight or branched alkyl group which contains or is interrupted by a cycloalkylene portion. Examples include the following:

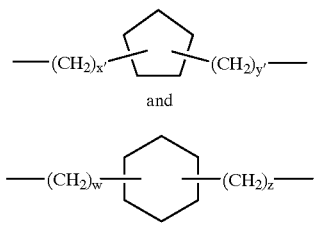

wherein: x' and y'=from 0–10; and w and z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

Heteroalkyl means an alkyl group containing from 2–15 carbon atoms and being interrupted by from 1–4 heteroatoms selected from O, S and N.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one to three groups, such as selected from halo, alkyl and trifluoromethyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydroimidazo[4,5-c] pyridine, phthalidyl and saccharinyl, as defined below.

Substituted alkyl, aryl and heteroaryl, and the substituted portions of aralkyl, aralkoxy, heteroaralkyl, heteroaralkoxy and like groups are substituted with from 1–3 groups selected from the group consisting of: halo, hydroxy, cyano, acyl, acylamino, aralkoxy, alkylsulfonyl, arylsulfonyl, alkylsulfonylamino, arylsulfonylamino, alkylaminocarbonyl, alkyl, alkoxy, aryl, aryloxy, aralkoxy, amino, alkylamino, dialkylamino, carboxy and sulfonylamino.

The terms "heterocycloalkyl" and "heterocyclyl" refer to a cycloalkyl group (nonaromatic) in which one of the carbon atoms in the ring is replaced by a heteroatom selected from O, S(O)y or N, and in which up to three additional carbon atoms may be replaced by said heteroatoms. When three heteroatoms are present in the heterocycle, they are not all linked together.

Examples of heterocyclyls are piperidinyl, morpholinyl, azetidinyl, pyrrolidinyl, tetrahydrofuranyl, imidazolinyl, piperazinyl, pyrolidin-2-one, piperidin-2-one and the like.

Acyl as used herein refers to —C(O)C$_{1-6}$ alkyl and —C(O)-aryl.

Acylamino refers to the group —NHC(O)C$_{1-6}$ alkyl and —NHC(O)aryl.

Aralkoxy refers to the group —OC$_{1-6}$ alkylaryl.

Alkaryl refers to C$_{1-6}$ alkyl-aryl-.

Alkylsulfonyl refers to the group —SO$_2$C$_{1-6}$ alkyl.

Alkylsulfonylamino refers to the group —NHSO$_2$C$_{1-6}$alkyl.

Arylsulfonylamino refers to the group —NHSO$_2$aryl.

Alkylaminocarbonyl refers to the group —C(O)NHC$_{1-6}$ alkyl.

Aryloxy refers to the group —O-aryl.

Sulfonylamino refers to the group —NHSO$_3$H.

Halo means Cl, F, Br and I selected on an independent basis.

Carbapenem I and II can be obtained as shown below in Flow Sheets A-1 and A-2

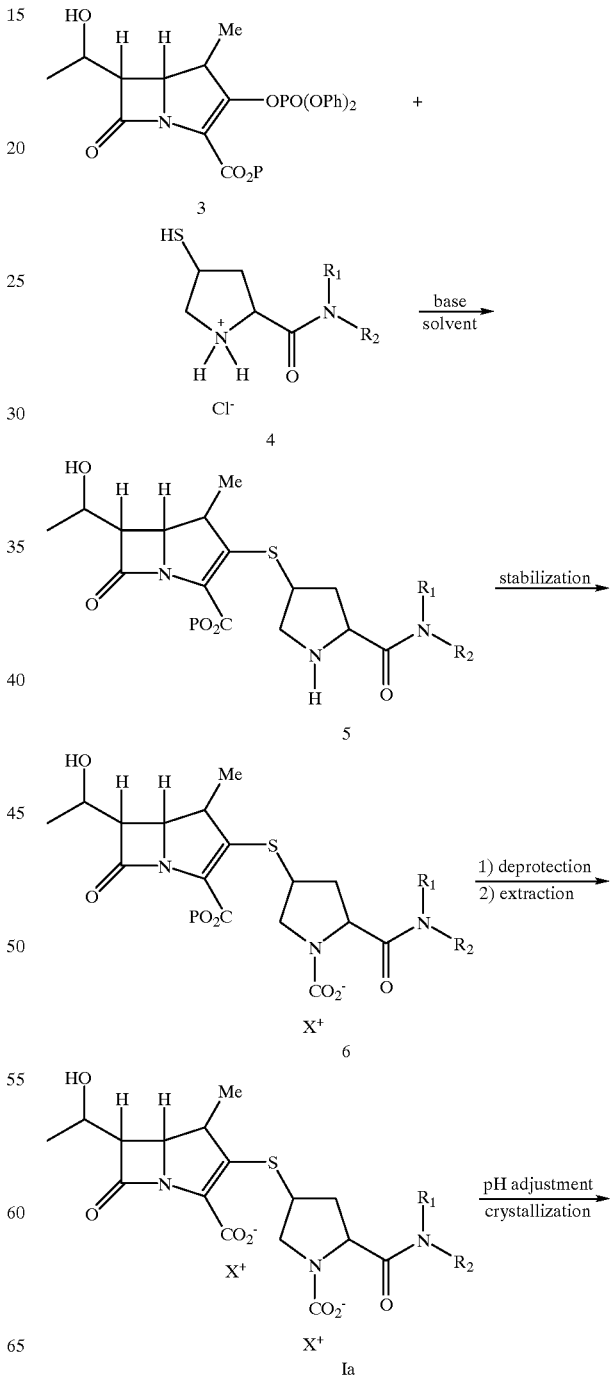

Flow Sheet A-1

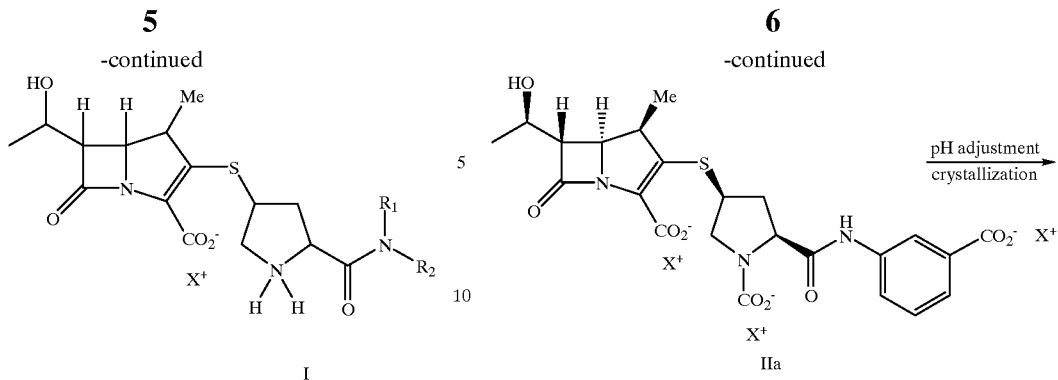

Flow sheet A-2 below provides a preferred process as it relates to 1β-methyl carbapenems.

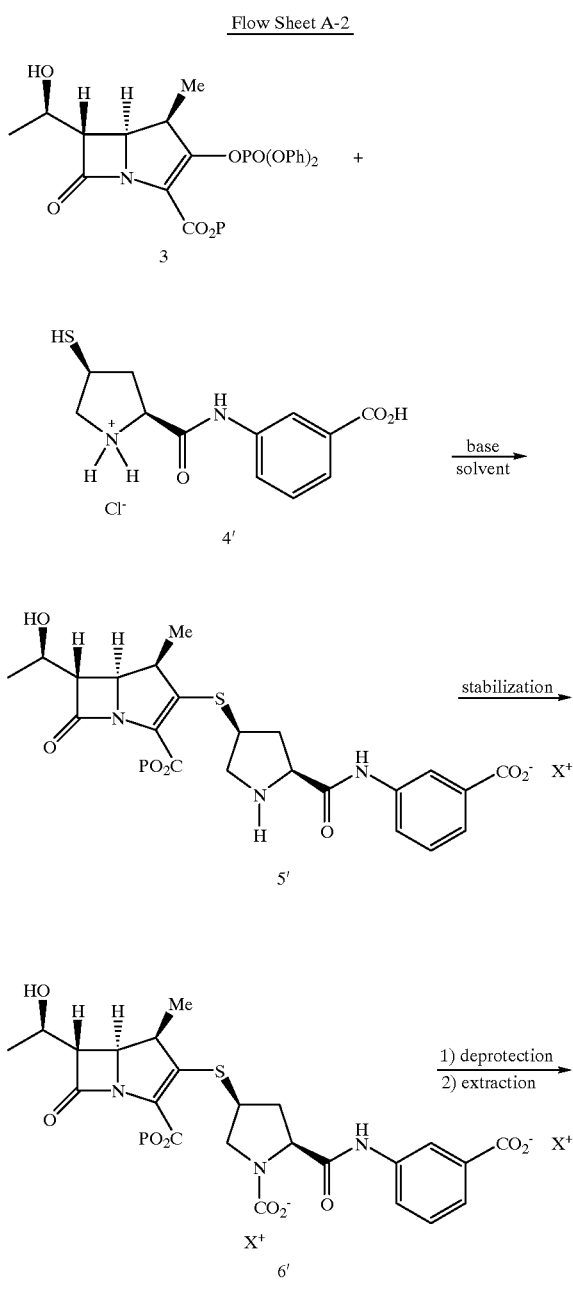

Compounds 3, 4 and 4' can be obtained in accordance with techniques such as those disclosed in U.S. Pat. No. 5,034,384, granted on Jul. 23, 1991; U.S. Pat. No. 4,994,568 granted on Feb. 19, 1991; U.S. Pat. No. 4,269,772 granted on May 26, 1981; U.S. Pat. No. 4,350,631 granted on Sep. 21, 1982; U.S. Pat. No. 4,383,946 granted on May 17, 1983; U.S. Pat. No. 4,414,155 granted on Nov. 8, 1983; U.S. Serial No. 60/052032 (our case 19995PV), filed Jul. 9, 1997; Tet. Let. 21, 2783 (1980); J. Am. Chem. Soc. 108, 6161 (1980); J. Am. Chem. Soc. 108, 4675 (1986) and U.S. Pat. No. 5,478,820 granted on Dec. 26, 1995. The teachings of these references are incorporated herein by reference. Compounds of formula I and Ia and derivatives thereof and processes thereof are disclosed in U.S. Ser. No. 08/887,849 (our case 19735), filed Jul. 3, 1997 and U.S. Serial No. 60/049640 (our case 19760PV), filed Jun. 16, 1997.

The compounds of formula 5 or 5' or salts thereof are produced by reacting the enol phosphate 3 and side chain precursor 4 or 4' in the presence of a base. This reaction is typically conducted at reduced temperature, e.g., about −30° C. to about −70° C., preferably about −40° C. to about −60° C. Bases which are suitable for the above reaction include organic as well as inorganic bases. Preferred bases for use herein are secondary and tertiary amines as diisopropylamine (DIPA), dicyclohexylamine (DCHA), 2,2,6,6-tetramethylpiperidine (TMP), guanidines such as 1,1,3,3-tetramethylguanidine (TMG), N,N,N',N'"-tetraethylcyclohexylguanidine (TECHG), N,N,N',N'-dicyclohexyldiethylguanidine (DCDEG) and amidines such as 1,8-diazabicyclo[4.3.0]undec-7-ene (DBU) and 1,5-diazabicyclo[4.3.0]non-5-ene (DBN). Most preferable bases are the guanidine bases and even more preferred is TMG.

The reaction can be conducted in an polar organic solvent, e.g., N-ethyl pyrrolidinone, N-methyl pyrrolidinone, N,N-dimethylformamide and the like. The preferred solvent is N-ethyl pyrrolidinone.

After coupling, the carbapenem is stabilized by combining the carbapenem with a carbon dioxide source. This provides a transient structure of formula 6 or 6' where X+ represents a charge balancing counterion and P a protecting group. Examples of carbon dioxide sources include carbon dioxide gas, bicarbonates, such as sodium and potassium bicarbonate, and carbonates such as sodium and potassium carbonate. Stabilization can be conducted according to the teachings in U.S. Serial No. 60/049640 (our case 19760PV), filed Jun. 16, 1997, incorporated by reference herein.

Stabilization can be conducted under substantially neutral to slightly basic conditions, e.g., about pH 7.0 to about 8.5.

After stabilization, the carbapenem is subject to deprotection, thus removing the 3-carboxyl protecting group. The pyrrolidine nitrogen is maintained in the carbamate form during deprotection yielding Ia or IIa.

A preferred deprotection reaction is hydrogenolysis, which can be conducted using hydrogen gas or a compound which forms hydrogen.

Hydrogenolysis effectively removes the protecting group from the 3-carboxylate without substantially disrupting the β-lactam ring or the stabilized carbamate form of the pyrrolidine amine.

Hydrogenolysis is typically conducted in the presence of a metal catalyst. The preferred reaction involves $H_2$ gas with a palladium (Pd/C) catalyst. If necessary, base can be added. A preferred base is sodium hydroxide or sodium bicarbonate.

The stability of the pyrrolidine N-carbamate is pH dependent. The carbamate is readily converted to the unsubstituted pyrrolidine amine or ammonium salt under neutral to mildly acidic conditions. The extractions are preferably carried out under neutral or weakly basic conditions in order to maintain the stabilizing presence of the carbamate according to the teachings of WO 9745430. After the extractions are completed the pH is adjusted to produce I or II which are directly crystallized.

Carbon dioxide sources, as used herein, refer to carbon dioxide gas as well as compounds which produce carbon dioxide upon dissolution. Representative examples include carbonates and bicarbonates, such as sodium carbonate, sodium bicarbonate, potassium carbonate and potassium bicarbonate. Preferably the carbonates and bicarbonates are used. Most preferably, the carbon dioxide source is sodium bicarbonate.

The carbon dioxide source can alternatively be included in the reaction medium prior to or during the deprotection reaction.

Other protecting groups which are readily removable, i.e., they can be removed, if desired, by procedures which will not cause cleavage or other disruption of the remaining portions of the molecule, can be used. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenolysis.

Examples of suitable 3-carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group is p-nitrobenzyl.

Many other suitable protecting groups are known in the art. See, e.g., T. W. Greene, *Protective Groups in Organic Synthesis*, John Wiley & Sons, Inc., 1981 (Chapters 2 and 5).

Numerous salt-forming ions are recited in Berge, S. M., et al. J. Pharm. Sci. 66(1): 1–16 (1977), the teachings of which are incorporated herein by reference. The charge balancing group X, maintains overall charge neutrality. Preferably X represents a pharmaceutically acceptable salt forming cation.

Preferred salt-forming cations are selected from the group consisting of: sodium, potassium, calcium and magnesium.

More preferably the salt forming cation is a member selected from the group consisting of: $Na^+$, $Ca^{+2}$ and $K^+$.

The salt forming cations mentioned above provide electronic balance and overall charge neutrality. From zero to three positively charged counterions may be present, depending upon the number of charged moieties on the carbapenem. This is largely a function of pH, since at low pH, protonation of the negatively charged moieties may occur. Different counterions may also be included in the overall composition. Hence, for example, calcium and sodium could be included together in the pharmaceutical composition to provide overall charge neutrality. The counterions can thus be varied within wide limits. Generally the counterion or counterions are pharmaceutically acceptable cationic species.

The compounds formed in the present invention have asymmetric centers and occur as racemates, racemic mixtures, and as individual diastereomers. The processes of synthesizing all such isomers, including optical isomers, are included in the present invention.

In a preferred aspect of the invention a process for synthesizing a compound of the formula II

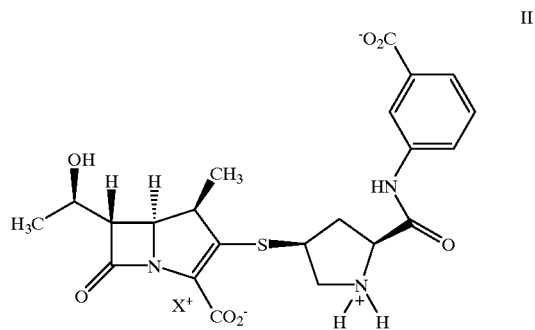

II or a pharmaceutically acceptable salt or ester thereof, is disclosed, wherein each $X^+$ represents a charge balancing group, comprising extracting a solution containing a crude compound of formula II or IIa

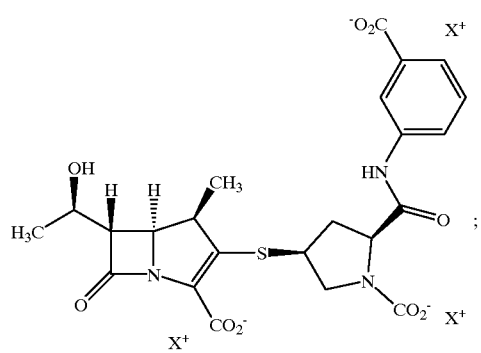

;

or a pharmaceutically acceptable salt thereof, wherein each $X^+$ is a charge balancing group, with an alcohol, collecting and crystallizing the resultant aqueous phase to produce a crystalline compound of formula II. It is preferable that the extraction is conducted in the presence of an ion-pairing reagent and that pH of the aqueous phase is maintained between neutral and mildly basic pH. It is also preferable that the extraction is performed while II is stabilized in the form of IIa.

The alcohol useful for the present invention includes, but is not limited to, iso-amyl alcohol, tert-amyl alcohol, 1-butanol, 2-butanol, 1-octanol, 1-hexanol, 1-heptanol, cyclohexanol, 1-pentanol, cyclopentanol, 2-pentanol, 2-methyl-1-pentanol, 2-ethyl-1-butanol, 4-methyl-2-pentanol, 2,6-dimethyl-4-heptanol, 2-methylcyclohexanol, preferably 1-butanol or iso-amyl alcohol.

Preferred ion-pairing reagents for use in the present invention are lipophilic carboxylic acids, phosphoric acids, phosphinic acids, sulfonic acids and the like and their salts. Most preferred ion-pairing reagents are the sodium salts of diphenylphosphoric acid, stearic acid or dodecylbenzenesulfonic acid.

Using the process described herein the elimination of chromatographic and nanofiltration steps results in significant productivity gains reducing the overall time cycle and minimizing losses to degradation. In addition, high capital expenditures associated with chromatographic and nanofiltration steps are averted.

The invention is illustrated in connection with the following non-limiting example.

EXAMPLE

Enolphosphate 3 (P=4-nitrobenzyl; 170 g) and sidechain 4' as its hydrochloride 1-butanol solvate (78 wt% ; 108 g) were dissolved in N-methyl pyrrolidinone (NEP) [1.5 L] and cooled to −55° C. TMG (110 g) was added slowly such that the temperature was maintained below −50° C. The mixture was aged at −50° C. for another hour to complete the reaction and then added to a solution of sodium bicarbonate (70 g) in water (1.8 L). The temperature and pH of the resulting solution were adjusted to 5° C. and 8.0, respectively, using carbon dioxide. The solution was hydrogenated in the presence of a Pd/C catalyst over a period of 1–4 hours allowing the temperature to rise from +5° C. to 20° C. Upon completion of the reaction the catalyst was filtered.

The filtrate (4 L at pH 7.5) was extracted at 0–5° C. with 12 L of a solution prepared by dissolving diphenyl phosphoric acid (333 g) and 50% sodium hydroxide (86 g) in a mixture of iso-amyl alcohol (19.1 L) and water (1.3 L). The aqueous layer (pH 7.0) was separated and further extracted with iso-amyl alcohol (16 L). The resulting aqueous layer (0.8–1.0 L; pH 8.0–8.5) was directly used for crystallization.

Using the above aqueous solution after the extractions, the pH was adjusted from 8.0–8.5 to 5.50 using glacial acetic acid and the product was crystallized by adding methanol and 1-propanol at −10° C., affording 90 g of the crystalline monosodium salt after filtration.

While certain preferred embodiments have been described herein in detail, numerous alternative embodiments are contemplated as falling within the scope of the appended claims.

What is claimed is:

1. A process for synthesizing a compound of the formula II

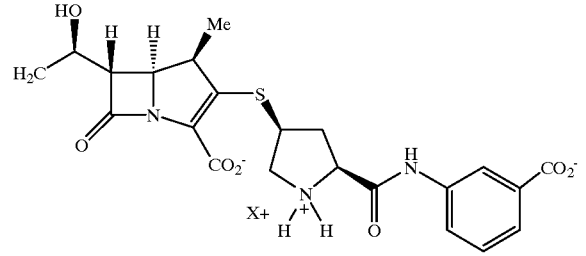

or a pharmaceutically acceptable salt thereof, wherein $X^+$ represents a charge balancing group of 1 positive charge to provide overall charge neutrality comprising deprotecting and extracting a polar organic solution containing a crude compound of formula 6'

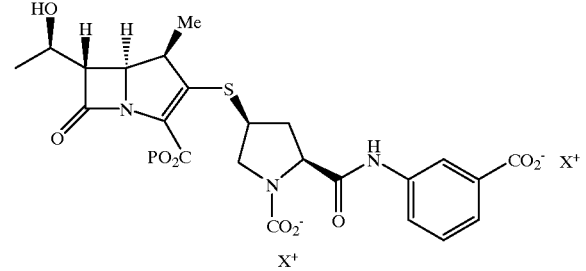

or a pharmaceutically acceptable salt thereof, with a $C_{4-10}$ alcohol, adjusting the pH to 5.5, collecting and crystallizing the resultant aqueous phase to produce a crystalline compound of II.

2. A process according to claim 1 wherein the extraction is conducted in the presence of an ion-pairing reagent belonging to the group consisting of lipophilic carboxylic acids, phosphoric acids, phosphinic acids, sulfonic acids or their salts.

3. A process in accordance with claim 2 wherein the polar organic solution consist in addition to the crude compound of formula 6 a polar organic solvent selected from the group consisting of N-ethyl pyrrolidinone, N-methyl pyrrolidinone, and N,N-dimethylformamide and the alcohol is selected from the group consisting of iso-amyl alcohol, tert-amyl alcohol, 1-butanol, 2-butanol, 1-octanol, 1-hexanol, 1-heptanol, cyclohexanol, 1-pentanol, cyclopentanol, 2-pentanol, 2-methyl-1-pentanol, 2-ethyl-1-butanol, 4-methyl-2-pentanol, 2,6-dimethyl-4-heptanol, and 2-methylcyclohexanol.

4. A process in accordance with claim 3 wherein the alcohol is iso-amyl alcohol or 1-butanol.

5. A process in accordance with claim 2 wherein ion-pairing reagent is a sodium salt of diphenylphosphoric acid, stearic acid or dodecylbenzenesulfonic acid.

6. A process for synthesizing a compound of the formula II

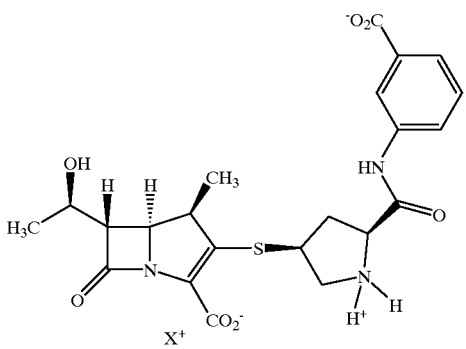

or a pharmaceutically acceptable salt thereof, is disclosed, wherein X⁺ represents a charge balancing group of 1 positive charge to provide overall charge neutrality comprising deprotecting and extracting a polar organic solution containing a crude compound of formula 6'

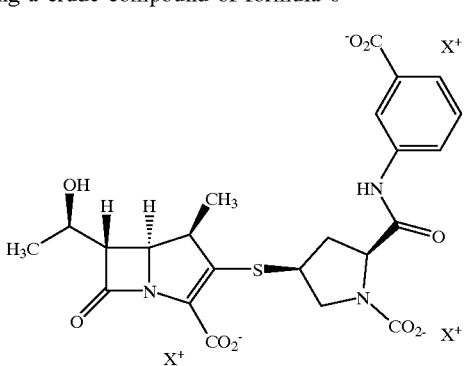

or a pharmaceutically acceptable salt thereof, with a $C_{4-10}$ alcohol, in the presence of an ion pairing reagent selected from the group consisting of phosphoric acids, phosphinic acids, stearic acids, sulfonic acids and salts thereof, adjusting the pH to 5.5, collecting and crystallizing the resultant aqueous phase to produce a crystalline compound of formula II.

7. A process in accordance with claim 6 wherein the polar organic solution consist in addition to the crude compound of formula 6 a polar organic solvent selected from the group consisting of N-ethyl pyrrolidinone, N-methyl pyrrolidinone, and N,N-dimethylformamide and the alcohol is selected from the group consisting of and the alcohol is selected from the group consisting of iso-amyl alcohol, tert-amyl alcohol, 1-butanol, 2-butanol, 1-octanol, 1-hexanol, 1-heptanol, cyclohexanol, 1-pentanol, cyclopentanol, 2-pentanol, 2-methyl-1-pentanol, 2-ethyl-1-butanol, 4-methyl-2-pentanol, 2,6-dimethyl-4-heptanol, or 2-methylcyclohexanol.

8. A process in accordance with claim 7 wherein the alcohol is iso-amyl alcohol or 1-butanol.

9. A process according to claim 6 wherein the extraction is conducted in the presence of an ion-pairing reagent belonging to the group consisting of carboxylic acids, phosphoric acids, phosphinic acids, sulfonic acids or their salts.

10. A process in accordance with claim 9 wherein the ion-pairing reagent is a sodium salt of diphenylphosphoric acid, stearic acid or dodecylbenzenes.

* * * * *

UNITED STATES PATENT AND TRADEMARK OFFICE
CERTIFICATE OF CORRECTION

PATENT NO.    : 6,504,027 B1                                              Page 1 of 1
DATED         : January 7, 2003
INVENTOR(S)   : John M. Williams et al.

It is certified that error appears in the above-identified patent and that said Letters Patent is hereby corrected as shown below:

<u>Title page,</u>
Item [54], Title, should read -- PROCESS FOR SYNTHESIZING CARBAPENEM ANTIBIOTICICS --

Signed and Sealed this

Second Day of December, 2003

JAMES E. ROGAN
*Director of the United States Patent and Trademark Office*